United States Patent

Yamada et al.

Patent Number: 5,569,796
Date of Patent: Oct. 29, 1996

[54] PROCESS FOR PRODUCING FLUORINATED SATURATED HYDROCARBON

[75] Inventors: Toshiro Yamada, Fujisawa; Yasuhiro Mitsuda, Yokohama, both of Japan

[73] Assignee: Nippon Zeon Co., Ltd., Tokyo, Japan

[21] Appl. No.: 406,904

[22] PCT Filed: Sep. 30, 1993

[86] PCT No.: PCT/JP93/01395

§ 371 Date: Mar. 29, 1995

§ 102(e) Date: Mar. 29, 1995

[87] PCT Pub. No.: WO94/07829

PCT Pub. Date: Apr. 14, 1994

[30] Foreign Application Priority Data

Sep. 30, 1992 [JP] Japan ................................. 4-285069

[51] Int. Cl.$^6$ .................................................. C07C 19/08
[52] U.S. Cl. .................................................. 570/175
[58] Field of Search ........................................ 570/175

[56] References Cited

U.S. PATENT DOCUMENTS 4,902,839  2/1990  Bielefeldt ........................ 570/175
4,954,666  9/1990  Bielefeldt ........................ 570/132

*Primary Examiner*—Alan Siegel
*Attorney, Agent, or Firm*—Armstrong, Westerman, Hattori, McLeland & Naughton

[57] ABSTRACT

A fluorinated saturated hydrocarbon represented by the formula (2):

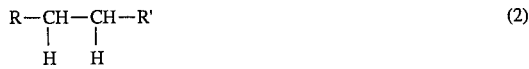

wherein R and R' represent a perfluoroalkyl group or both R and R' are bonded together to form a perfluoroalkylene group which is a part of a ring, is industrially advantageously produced with good operating characteristics by reacting a fluorinated unsaturated hydrocarbon represented by the formula (1):

$$R-CF=CF-R' \quad (1)$$

wherein R and R' are as defined above, with hydrogen in the presence of a platinum catalyst.

10 Claims, No Drawings

PROCESS FOR PRODUCING FLUORINATED SATURATED HYDROCARBON

TECHNICAL FIELD

This application is a 371 of PCT/JP93/01395 filed Sep. 30, 1993.

This invention relates to a process for producing a fluorinated saturated hydrocarbon.

BACKGROUND ART

Chloro Fluoro Carbons (CFCs) have heretofore been used as a detergent and a refrigeration medium. However, in recent years, an increasing attention has been paid to a problem of pollution nuisance in a global environment and restriction of the use of CFCs has been universally acceded to. Therefore, alternatives of CFCs have been intensively investigated and developed. Especially chlorine-free fluorinated saturated hydrocarbons attract public attention from a viewpoint of environmental protection because there is no problem of depletion of the ozone layer.

For example, fluorinated saturated hydrocarbons represented by the following formula (2):

$$R-CH(H)-CH(H)-R' \quad (2)$$

wherein R and R' represent a perfluoroalkyl group, or both R and R' are bonded together to form a perfluoroalkylene group which is a part of a ring, are expected to be used as detergents, solvents, propellants, and heating media for heat pumps. As a specific example of the fluorinated saturated hydrocarbons, 1,1,2,2,3,3-hexafluorocyclopentane is described as a detergent in U.S. Pat. No. 5,084,199.

As means for producing fluorinated saturated hydrocarbons which are expected to be widely used in future, a process is generally known wherein a corresponding unsaturated hydrocarbon having chlorine or bromine bonded to the carbon-to-carbon double bond is allowed to react with hydrogen in the presence of a base such as a basic alkali metal salt or amine by using a palladium catalyst or a nickel catalyst (for example, DE-A-3,735,467 and U.S. Pat. No. 5,084,199). As specific example of such process, there can be mentioned a process wherein 1,2-dichloro- 3,3,4,4,5,5-hexafluoro-cyclopentene is hydrogenated in the presence of triethylamine by using a Raney nickel catalyst to produce 1,1,2,2,3,3-hexafluorocyclopentane, and a process wherein 1,2-dichloro-3,3,4,4,5,5-hexafluoro-cyclopentene is hydrogenated in the presence of sodium acetate by using a palladium catalyst to produce 1,1,2,2,3,3-hexafluorocyclopentane. However, these processes have problems in economy and operating characteristics because acidic substances such as hydrogen chloride or hydrogen bromide produced as by-products are deposited as an alkali metal salt or an amine salt and thus an operation of separating the target substance is indispensable.

DISCLOSURE OF INVENTION

To solve the problems of the prior art, the inventors conducted researches and found that, where a fluorinated unsaturated hydrocarbon represented by the formula (1) shown below is reacted with hydrogen by using a platinum catalyst, a fluorinated saturated hydrocarbon represented by the formula (2) shown below can be produced in a high yield; that, since a basic substance is not used, hydrogen fluoride produced by a side reaction can be separated from the target substance only by a distillation procedure; and further that the recovered hydrogen fluoride can be effectively utilized as a raw material for other reactions. The present invention has been completed on the basis of these findings.

In accordance with the present invention, there is provided a process for producing a fluorinated saturated hydrocarbon represented by the formula (2):

$$R-CH(H)-CH(H)-R' \quad (2)$$

wherein R and R' represent a perfluoroalkyl group or both R and R' are bonded together to form a perfluoroalkylene group which is a part of a ring, which comprises reacting a fluorinated unsaturated hydrocarbon represented by the formula (1):

$$R-CF=CF-R' \quad (1)$$

wherein R and R' are as defined above, with hydrogen in the presence of a platinum catalyst.

BEST MODE FOR CARRYING OUT THE INVENTION

The starting compound used in the present invention is a fluorinated unsaturated hydrocarbon represented by the above-mentioned formula (1). As examples of R and R', there can be mentioned a perfluoroalkyl group having 1 to 4 carbon atoms such as a trifluoromethyl group, a pentafluoroethyl group, a heptafluoro-n-propyl group, a heptafluoroisopropyl group, a nonafluoro-n-butyl group, a nonafluoroisobutyl group, or a nonafluoro-tert-butyl group, and a perfluoroalkylene group having 2 to 8 carbon atoms which is a part of a ring and which is formed by both R and R'. R and R' preferably have 1 to 3 carbon atoms.

The platinum catalyst is conventionally used for a hydrogenation reaction and includes, for example, a catalyst having platinum supported on a carrier, and a platinum-compound catalyst. The catalyst having platinum supported on a carrier is not particularly limited provided that platinum is supported in a conventional manner on a carrier such as activated carbon, alumina or silica. The amount of platinum is usually in the range of 0.1 to 10% by weight based on the weight of the carrier. The platinum-supported catalyst may be hydrated and the content of water is usually about 50% by weight. The platinum compound in the platinum-compound catalyst includes, for example, platinum oxide, colloidal platinum and platinum black.

The amount of the platinum catalyst is usually selected in the range of $10^{-6}$ to 10% by weight, preferably $10^{-5}$ to $10^{-2}$% by weight, as the amount of platinum or platinum compound, based on the weight of the fluorinated unsaturated hydrocarbon.

A solvent can be used for the hydrogenation reaction according to the need. The solvent used is not particularly limited provided that it is inactive for the reaction. As specific examples of the solvent, there can be mentioned alcohols such as ethanol, methanol and isopropanol, aliphatic hydrocarbons such as n-pentane and n-hexane, alicyclic hydrocarbons such as cyclopentane and cyclohexane, esters such as ethyl acetate and butyl acetate, ethers such as diethyl ether, tetrahydrofuran and 1,4-dioxane, and ketones such as acetone and methyl ethyl ketone.

The reaction temperature is usually in the range of 0° to 200° C., preferably 20° to 150° C. The reaction time is usually in the range of 0.5 to 15 hours, preferably 0.5 to 10 hours. The reaction pressure varies depending upon the particular raw materials used, reaction temperature and other conditions, but usually the reaction is carried out under a pressure of about 1 to 50 kg/cm² in an enclosed reactor.

The procedure by which the reaction is carried out is not particularly limited. For example, a procedure can be employed wherein an enclosed reactor such as an autoclave is charged with a fluorinated unsaturated hydrocarbon and a platinum catalyst, hydrogen of a predetermined pressure is introduced into the reactor, and the content is maintained at a predetermined temperature to effect the reaction.

The amount of hydrogen consumed for the reaction is theoretically three times in moles of the amount of the fluorinated unsaturated hydrocarbon. Undesirable side reactions do not take place in the process of the present invention, and therefore, there is no need of introducing an excessive amount of hydrogen. Hydrogen may be introduced in an amount sufficient for replenishing the consumed amount.

After the completion of reaction, the platinum catalyst is removed from the reaction liquid and the reaction liquid is then subjected to distillation whereby a fluorinated saturated hydrocarbon can be separated.

The process of the present invention is characterized in that a fluorinated unsaturated hydrocarbon of the formula (1) is reacted with hydrogen in the presence of a platinum catalyst to allow both dehalogenation and hydrogenation to occur whereby a fluorinated saturated hydrocarbon of the formula (2) can be obtained in a high yield and by a procedure which is economically advantageous and is of a good operatability. In contrast, if a nickel catalyst or a catalyst of another metal analogous to platinum, such as palladium, rhodium or ruthenium, is used, then the addition reaction of hydrogen to a carbon-to-carbon double bond predominantly occurs and it becomes difficult to produce the target fluorinated saturated hydrocarbon with an enhanced selectivity.

Further, a basic substance is not used in the present invention, and therefore, hydrogen fluoride produced does not form a salt and can be easily recovered by distillation.

The invention will now be described specifically by the following examples. In the examples and comparative examples, parts and % are by weight unless otherwise specified.

EXAMPLE 1

A stainless steel autoclave, the inner wall of which was lined with a fluoroplastic, was charged with 5.0 g of perfluorocyclopentene and 0.5 g of a catalyst comprising 2% by weight of platinum supported on activated carbon and having a water content of 50%. Hydrogen gas was introduced into the autoclave so that the pressure reached 5 kg/cm². The temperature was elevated to 40° C. with stirring and the reaction was conducted at that temperature while hydrogen was replenished for the consumed hydrogen. When 7 hours elapsed, the consumption of hydrogen ceased and thus the reaction was completed. Then the catalyst was removed from the reaction mixture and the reaction mixture was distilled whereby 4.2 g of 1,1,2,2,3,3-hexafluorocyclopentane having a purity of 84% was obtained. The yield was 89%.

EXAMPLE 2

By the same procedure as described in Example 1, the hydrogenation reaction was conducted wherein 0.25 g of a catalyst (dry state) comprising 2% by weight of platinum supported on alumina was used instead of the catalyst used in Example 1. 1,1,2,2,3,3-Hexafluorocyclopentane was obtained in a yield of 89%.

EXAMPLE 3

By the same procedure as described in Example 1, the hydrogenation reaction was conducted wherein 0.25 g of a catalyst (dry state) comprising 2% by weight of platinum supported on silica was used instead of the catalyst used in Example 1. 1,1,2,2,3,3-Hexafluorocyclopentane was obtained in a yield of 84%.

EXAMPLE 4

By the same procedure as described in Example 1, the hydrogenation reaction was conducted wherein perfluoro-2-butene was used instead of the perfluorocyclopentene. 1,1,1,4,4,4-Hexafluorobutane was obtained in a yield of 86%.

COMPARATIVE EXAMPLE 1

By the same procedure as described in Example 1, the hydrogenation reaction was conducted wherein 0.25 g of a catalyst (dry state) comprising 5% by weight of palladium supported on activated carbon was used instead of the catalyst used in Example 1. 1,1,2,2,3,3-Hexafluorocyclopentane was not obtained, but 1,2,3,3,4,4,5,5-octafluorocyclopentane was obtained in a yield of 93%.

COMPARATIVE EXAMPLE 2

By the same procedure as described in Example 1, the hydrogenation reaction was conducted wherein a catalyst (dry state) comprising 5% by weight of nickel supported on alumina was used instead of the catalyst used in Example 1. 1,1,2,2,3,3-Hexafluorocyclopentane was not obtained, but 1,2,3,3,4,4,5,5-octafluorocyclopentane was obtained in a yield of 88%.

COMPARATIVE EXAMPLE 3

By the same procedure as described in Example 1, the hydrogenation reaction was conducted wherein 0.5 g of a catalyst comprising 5% by weight of rhodium supported on activated carbon and having a water content of 50% was used instead of the catalyst used in Example 1. Analysis of the reaction product by gas chromatography revealed that the product was composed of 10% of 1,1,2,2,3,3-hexafluorocyclopentane, 38% of 1,1,2,2,3,3,4-heptafluorocyclopentane and 39% of 1,1,2,2,3,3,4,5-octafluorocyclopentane.

COMPARATIVE EXAMPLE 4

By the same procedure as described in Example 1, the hydrogenation reaction was conducted wherein 0.5 g of a catalyst comprising 5% by weight of ruthenium supported on activated carbon and having a water content of 50% was used instead of the catalyst used in Example 1. Analysis of the reaction product by gas chromatography revealed that the product was composed of 28% of 1,1,2,2,3,3-hexafluorocyclopentane, 42% of 1,1,2,2,3,3,4-heptafluorocyclopentane and 26% of 1,1,2,2,3,3,4,5-octafluorocyclopentane.

COMPARATIVE EXAMPLE 5

By the same procedure as described in Example 4, the hydrogenation reaction was conducted wherein 0.5 g of a catalyst (dry state) comprising 5% by weight of palladium supported on activated carbon was used instead of the catalyst used in Example 4. Analysis of the reaction product by gas chromatography revealed that the product did not contain 1,1,1,4,4,4-hexafluorobutane, but was a mixture of a diastereomer of 1,1,1,2,3,4,4,4-octafluorobutane and a minor amount of 1,1,1,2,4,4,4-heptafluorobutane.

INDUSTRIAL APPLICABILITY

By the process of the present invention, a fluorinated saturated hydrocarbon represented by the formula (2) can be industrially advantageously produced with good operating characteristics.

This fluorinated saturated hydrocarbon does not cause depletion of the ozone layer and is advantageous from a view-point of environmental protection. Therefore, it is useful, for example, as a detergent, a solvent, a refrigeration medium, a heating medium and a propellant.

We claim:

1. A process for producing a fluorinated saturated hydrocarbon represented by the formula (2):

wherein R and $R^1$ represent a perfluoroalkyl group or both R and $R^1$ are bonded together to form a perfluoroalkylene group which is a part of a ring, which comprises reacting a fluorinated unsaturated hydrocarbon represented by the formula (1):

wherein R and $R^1$ are as defined above, with hydrogen in the presence of a platinum catalyst and in the absence of a base.

2. A process for producing a fluorinated saturated hydrocarbon according to claim 1, wherein R and R' in the formulae represent a perfluoroalkyl group having 1 to 4 carbon atoms or both R and R' are bonded together to form a perfluoroalkylene group having 2 to 8 carbon atoms which is a part of a ring.

3. A process for producing a fluorinated saturated hydrocarbon according to claim 1, wherein the platinum catalyst is a platinum-supported catalyst comprising platinum supported on a carrier, or a platinum compound catalyst.

4. A process for producing a fluorinated saturated hydrocarbon according to claim 3, wherein the carrier is selected from the group consisting of activated carbon, alumina and silica.

5. A process for producing a fluorinated saturated hydrocarbon according to claim 3, wherein the amount of the platinum supported in the platinum-supported catalyst is in the range of 0.1 to 10% by weight based on the weight of the carrier.

6. A process for producing a fluorinated saturated hydrocarbon according to claim 3, wherein the platinum compound is selected from the group consisting of platinum oxide, colloidal platinum and platinum black.

7. A process for producing a fluorinated saturated hydrocarbon according to any claim, wherein the amount of the platinum catalyst is in the range of 10 to 10% by weight as the amount of platinum or platinum compound, based on the weight of the fluorinated unsaturated hydrocarbon.

8. A process for producing a fluorinated saturated hydrocarbon according to claim 1, wherein the hydrogenation reaction is carried out in the presence of a solvent selected from the group consisting of alcohols, aliphatic hydrocarbons, alicyclic hydrocarbons, esters, ethers and ketones.

9. A process for producing a fluorinated saturated hydrocarbon according to claim 1, wherein the reaction temperature is in the range of 0° to 200° C. and the reaction time is in the range of 0.5 to 15 hours.

10. A process for producing a fluorinated saturated hydrocarbon according to claim 1, wherein the hydrogenation reaction is carried out at a pressure of 1 to 50 kg/cm² in an enclosed reactor.

* * * * *